US00PP23981P2

(12) United States Plant Patent
Judd

(10) Patent No.: US PP23,981 P2
(45) Date of Patent: Oct. 8, 2013

(54) ***VERBASCUM* PLANT NAMED 'BLUE LAGOON'**

(50) Latin Name: *Verbascum luridiflorum*
Varietal Denomination: Blue Lagoon

(75) Inventor: Nigel Judd, Ipswich (GB)

(73) Assignee: T.I.P.S (The International Plant Source), Noordwiskerhout (NL)

( * ) Notice: Subject to any disclaimer, the term of this patent is extended or adjusted under 35 U.S.C. 154(b) by 16 days.

(21) Appl. No.: 13/506,768

(22) Filed: May 16, 2012

(51) Int. Cl.
*A01H 5/00* (2006.01)

(52) U.S. Cl.
USPC ..... Plt./489

(58) Field of Classification Search
USPC ..... Plt./489
See application file for complete search history.

*Primary Examiner* — Kent L Bell
(74) *Attorney, Agent, or Firm* — Penny J. Aguirre

(57) ABSTRACT

A new cultivar of *Verbascum*, 'Blue Lagoon', characterized by its flowers that are clear blue in color, its tall, strong flowering stems, its strong and healthy growth habit, and its very floriferous plant habit.

2 Drawing Sheets

Botanical classification: *Verbascum luridiflorum.*
Cultivar designation: 'Blue Lagoon'.

BACKGROUND OF THE INVENTION

The present invention relates to a new and distinct cultivar of *Verbascum luridiflorum* plant known as 'Blue Lagoon' and will be referred to hereafter by its cultivar name, 'Blue Lagoon'. The new cultivar represents a new herbaceous perennial grown for landscape use.

The new cultivar was derived from a controlled breeding program conducted by the Inventor in Harkstead, Ipswich, Suffolk, United Kingdom. The overall objective of the breeding program was to create a cultivar of *Verbascum* that has a strong plant and growth habit combined with blue flowers. 'Blue Lagoon' was selected in September of 2009 as a single unique plant from amongst the seedlings derived from a cross made in summer of 2008 between two unnamed, proprietary plants of the Inventor as the parents; the female parent designated as VS08028 and the male parent designated as VS07035.

Asexual reproduction of the new cultivar was first accomplished by in vitro propagation under the direction of the Inventor in Harkstead, Ipswich, Suffolk, United Kingdom in summer of 2009. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Blue Lagoon' as a unique cultivar of *Verbascum.*

1. 'Blue Lagoon' exhibits flowers that are clear blue in color.
2. 'Blue Lagoon' exhibits tall, strong stems.
3. 'Blue Lagoon' exhibits a strong and healthy growth habit.
4. 'Blue Lagoon' exhibits a very floriferous plant habit.

The female parent of 'Blue Lagoon', VS08028 differs from 'Blue Lagoon' in having flowers that are bluish green in color.

The male parent of 'Blue Lagoon', VS07035, differs from 'Blue Lagoon' in having flowers that are deep violet in color. 'Blue Lagoon' can be most closely compared to the cultivars 'Lavender Lass' (U.S. Plant Pat. No. 16,658) and 'Blue Pixie' (not patented). 'Lavender Lass' differs from 'Blue Lagoon' in having much shorter stems and in having flowers that are lavender-mauve in color. 'Blue Pixie' differs from 'Blue Lagoon' in having much shorter stems and in having flowers that are purple-blue in color.

BRIEF DESCRIPTION OF THE DRAWING

The accompanying colored photographs illustrate the overall appearance and distinct characteristics of the new *Verbascum*. The photographs were taken of plants about 4 months in age as grown in 11-cm containers in a greenhouse in Noordwijkerhout, The Netherlands.

The photograph in FIG. 1 shows the strong, tall flowering stems of 'Blue Lagoon'.

Figure 1:
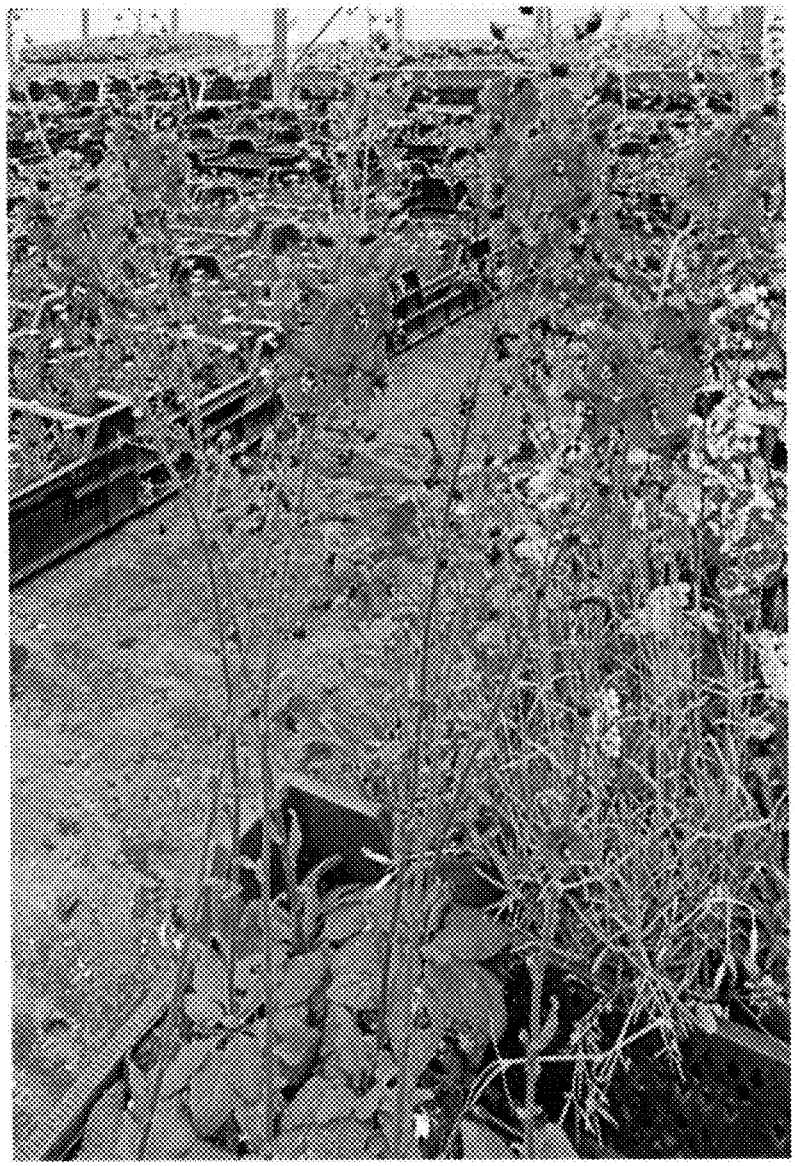
Figure 2:
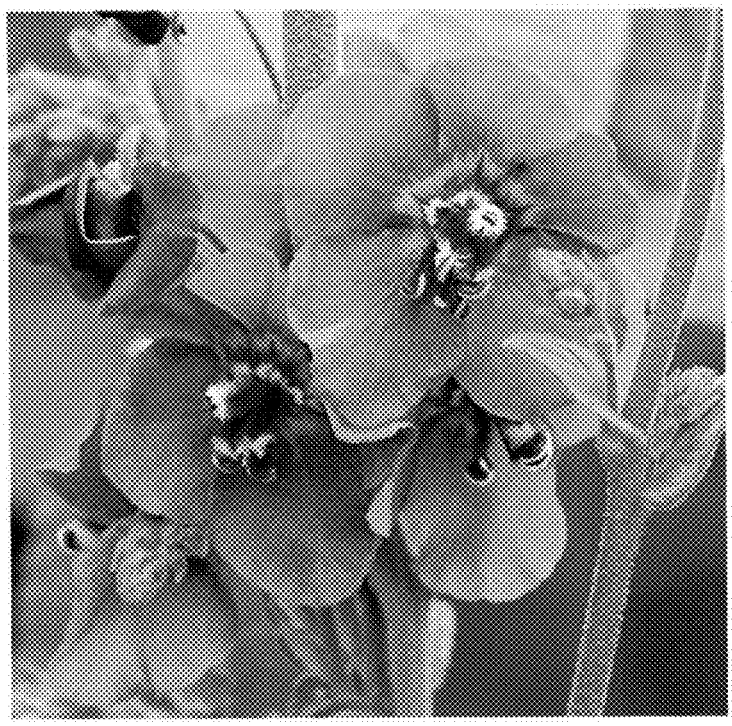

The photograph in FIG. 2 provides a close-up view of the flowers of 'Blue Lagoon'.

Figure 3:
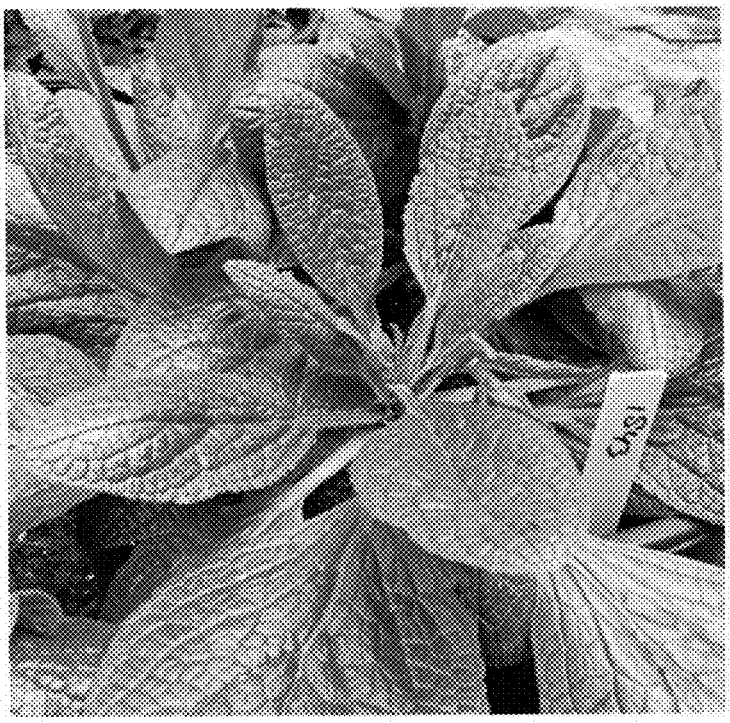

The photograph in FIG. 3 provides a close-up view of the healthy foliage of 'Blue Lagoon'. The colors in the photograph may differ slightly from the color values cited in the detailed botanical description, which accurately describe the colors of the new *Verbascum.*

DETAILED BOTANICAL DESCRIPTION OF THE PLANT

The following is a detailed description of 15 week-old plants of the new cultivar as grown in 11-cm containers in a greenhouse in Noordwijkerhout, the Netherlands. Plants were grown under average day temperatures of 16° to 28° C. and average night temperatures of 8° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—June through September in the United Kingdom.

*Plant habit*.—Herbaceous perennial, clump-forming, upright flower scapes arise from a rosette of basal foliage, moderate growth rate.

*Height and spread*.—Reaches about 87.5 cm in height and 19.5 cm in width (4-months in age) and reaches about 150 cm in height and 50 cm in width in the landscape.

*Cold hardiness*.—At least to U.S.D.A. Zone 7.

*Diseases and pests*.—No pests and diseases problems have been observed, plants have been observed to be healthy.

*Root description*.—Fibrous.

*Growth rate*.—Moderate.

Stem description:

*Stem size*.—About 20 cm in length and 3.5 mm in width.

*Stem shape*.—Round.

*Stem color*.—144A.

*Stem surface*.—Dull, covered with short hairs, 0.3 mm in length and 157D in color.

*Stem strength*.—Strong.

*Stem aspect*.—Slightly angled, stems grow in an average angle of 90° (vertical) to soil level.

Foliage description:

*Leaf shape*.—Ovate.

*Leaf division*.—Single.

*Leaf base*.—Short attenuate.

*Leaf apex*.—Bluntly acute.

*Leaf venation*.—Pinnate, color: upper surface; 144A, lower surface; 146D.

*Leaf margins*.—Crenate.

*Leaf attachment*.—Petiolate.

*Leaf arrangement*.—Alternate, in basal rosette.

*Leaf surface*.—Upper and lower surfaces; rugose, moderately glossy and covered with very short pubescent hairs; 0.5 mm in length and 157D in color.

*Leaf color*.—Immature upper and lower surfaces; 143C, mature upper surface; N137B, mature lower surface; 138A to 138B.

*Leaf size*.—Average of rosette leaves; 7.1 cm in length and 4.7 cm in width, average of stem leaves; 6 cm in length and 2.6 cm in width.

*Leaf quantity*.—Average of 12 leaves per rosette and an average of 7 stem leaves.

*Petiole size*.—Average of rosette leaves; 1.6 cm in length, 0.5 cm in diameter and 0.3 cm in height, average of stem leaves; 0.5 cm in length, 0.5 cm in diameter and 0.2 cm in height.

*Petiole color*.—Upper and lower surfaces 146B, slightly tinged with N186C.

Flower description:

*Inflorescence type*.—Racemes on flower scapes arising from basal foliage.

*Lastingness of inflorescence*.—About 10 days after the first bloom opens. Self-cleaning.

*Inflorescence size*.—About 67.5 cm in height and 5.4 cm in width.

*Flower size*.—About 2.7 cm in height and 0.9 cm in width.

*Flower form*.—Rotate.

*Flower fragrance*.—None.

*Flower number*.—About 110 per raceme.

*Peduncle size*.—Average of 67 cm in length, 0.2 cm in diameter.

*Peduncle shape*.—Round.

*Peduncle color*.—Upper and lower surface; 144A.

*Peduncle angle*.—Average angle of 90° (vertical) to soil level.

*Peduncle strength*.—Strong.

*Pedicel size*.—About 1.6 cm in length and 5 mm in diameter.

*Pedicel shape*.—Round.

*Pedicel angle*.—Average angle of 55° to peduncle.

*Pedicel color*.—143B.

*Flower bud size*.—Up to 0.5 cm in length and 0.8 cm in diameter.

*Flower bud color*.—103B.

*Flower bud shape*.—Flattened pentagonal.

*Flower type*.—Rotate and outward facing.

*Calyx form*.—Rotate.

*Calyx size*.—About 0.4 cm in length, 0.7 cm in diameter.

*Sepal number*.—5.

*Sepal size*.—About 0.4 cm in length, 1.5 mm in width.

*Sepal apex*.—Acute.

*Sepal base*.—Broad cuneate.

*Sepal shape*.—Elliptic.

*Sepal margin*.—Entire.

*Sepal surface*.—Upper and lower surface dull, lower surface densely covered with very short glandular hairs.

*Sepal color*.—Immature and mature upper and lower surfaces; 143B.

*Corolla features*.—Petals distinct but fused at base to a short tube, 5 mm in length, 144D in color, petals overlap near the proximal region, petals broadly flaring with reflexed edges creating a wavy appearance.

*Petal number*.—5.

*Petal size*.—About 1.2 cm in length, 1.2 cm in width.

*Petal shape*.—Orbicular.

*Petal color*.—Upper surface when opening; 103B to 103C, lower surface when opening; 103D, upper surface when fully opened; between 102B and 103D, lower surface when fully opened; 102C, fading to 102A.

*Petal surface*.—Dull and smooth.

*Petal margins*.—Entire, sinuate.

*Petal apex*.—Rounded.

Reproductive organs:

*Gynoecium*.—1 Pistil, 0.8 cm in length, style is 0.75 cm in length and N92A in color; stigma club-shaped and 160C in color, ovary is 143C in color.

*Androcoecium*.—5 stamens, anthers; dorsifixed, 0.2 mm in length and N79B, filament is 0.8 cm in length, covered with short hairs N79B in color, pollen is low in quantity and 25A in color.

*Fruit*.—No fruit or seeds detected to date.

It is claimed:

1. A new and distinct cultivar of *Verbascum* plant named 'Blue Lagoon' as herein illustrated and described.

* * * * *